United States Patent [19]

Cordier

[11] Patent Number: 4,495,368

[45] Date of Patent: Jan. 22, 1985

[54] PROCESS FOR THE PREPARATION OF META-HALOGENOANILINES

[75] Inventor: Georges Cordier, Francheville, France

[73] Assignee: Rhone-Poulenc Agrochimie, Lyons, France

[21] Appl. No.: 462,327

[22] Filed: Jan. 31, 1983

[30] Foreign Application Priority Data

Feb. 5, 1982 [FR] France .................. 82 02021

[51] Int. Cl.$^3$ .................. C07C 85/00; C07C 85/24
[52] U.S. Cl. .................. 564/412
[58] Field of Search .................. 564/412

[56] References Cited

U.S. PATENT DOCUMENTS

| | | | |
|---|---|---|---|
| 4,206,147 | 6/1980 | Daumes et al. | 564/412 |
| 4,206,148 | 6/1980 | Biola et al. | 564/412 |
| 4,324,914 | 4/1982 | Cordier | 564/412 |
| 4,340,759 | 7/1982 | Cordier | 564/412 |
| 4,351,959 | 9/1982 | Cordier | 564/412 |

*Primary Examiner*—Paul F. Shaver

*Attorney, Agent, or Firm*—Robert E. Burns; Emmanuel J. Lobato; Bruce L. Adams

[57] ABSTRACT

Process for the preparation of anilines substituted in the meta-position by a halogen atom.

An aniline of the formula:

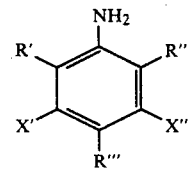

in which: X' and X", R', R" and R''' are a halogen atom, alkyl ($C_1$–$C_4$) or alkoxy ($C_1$–$C_4$), one of the symbols X and one of the symbols R necessarily being a halogen and it being possible for one of the symbols X and one of the symbols R to be a hydrogen atom, is subjected to catalytic hydrogenation, in an anhydrous organic liquid phase, namely a chlorobenzene phase, in the presence of a halogen-containing hydracid and of a noble metal from group VIII of the periodic classification.

26 Claims, No Drawings

PROCESS FOR THE PREPARATION OF META-HALOGENOANILINES

The present invention relates to a process for the preparation of anilines substituted by a halogen in the meta-position, by reacting hydrogen with aromatic amino compounds which are more highly halogen-substituted. These meta-halogenoanilines are intermediates, in particular for the manufacture of plant-protection products.

The preparation of chloroanilines substituted in the meta-position by reacting polychloroanilines with hydrogen under pressure, in an acid medium, in the presence of a catalyst based on a noble metal, has been described in French Pat. No. 2,298,531. The process described, however, requires the use of high pressures and of very large amounts of hydrochloric acid, which presents serious corrosion problems.

The object of the present invention is precisely to prepare meta-substituted halogenoanilines by the selective hydrodechlorination of polyhalogenoanilines without corrosion problems.

The invention relates more particularly to a process for the preparation of anilines substituted in the meta-position by a halogen atom, by the catalytic hydrogenation, in an anhydrous organic liquid phase, in the presence of an acid, under the action of heat and under pressure, and in the presence of noble metals from group VIII of the periodic classification, of amine-substituted and chlorine-substituted benzene derivatives of the formula:

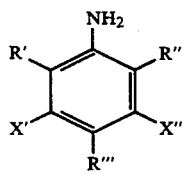
(I)

in which:

X' and X", which are identical to or different from one another, each represent a halogen atom, preferably a chlorine atom, an alkyl radical having 1 to 4 carbon atoms or an alkoxy radical having 1 to 4 carbon atoms, at least one of X' and X" necessarily being a halogen atom, preferably a chlorine atom, and it also being possible for one of X' and X" to be hydrogen, and R', R" and R''', which are identical to or different from one another, each represent a halogen atom, preferably a chlorine atom, an alkyl radical having 1 to 4 carbon atoms, alkoxy radical having 1 to 4 carbon atoms, an optionally substituted benzyl radical or phenyl radical or an optionally substituted phenoxy radical, at least one of these three symbols representing the halogen atom, preferably the chlorine atom, and it also being possible for at most two of R', R" or R''' to be hydrogen, wherein the reaction is carried out in the presence of a hydracid, in particular a halogen-containing hydracid, in a chlorobenzene solvent.

The term "halogen-containing hydracid" is understood as meaning an anhydrous hydracid containing a halogen atom such as chlorine and, preferably, bromine and iodine.

This acid can be added as such as soon as the reaction has started, or in the form of a generator which releases the acid gradually under the reaction conditions. As the generator, it is preferred to use the halogen corresponding to the acid or an alkali metal halide or quaternary ammonium halide.

This acid or its generator, in the form of an essentially anhydrous liquid or a gas, which is soluble in the medium, is added in an amount, depending on the nature of the acid, which is such that the molar ratio to the starting polychloroaniline is generally between 1/100 and 10/1 and preferably between 1/10 and 5/1.

The process according to the invention is carried out in a homogeneous anhydrous organic liquid phase (except, of course, for the catalyst based on a noble metal) consisting of a solution, under the reaction conditions, of the starting polychloroaniline in an inert solvent or mixture of inert solvents of the chlorobenzene type. Any chlorobenzenes which are liquid under the reaction conditions, i.e. mono-, di-, tri-, tetra- and pentachlorobenzenes, are suitable, but, for greater convenience, the preferred chlorobenzenes are those which are liquid at ambient temperature, namely monochlorobenzene, 1,2-dichlorobenzene, 1,3-dichlorobenzene and 1,2,4-trichlorobenzene.

The pressure at which the reaction is carried out is generally greater than 5 bars (relative pressure). There is no critical upper limit to the pressure, but, for economic reasons, it is advantageous to carry out the reaction at pressures of less than 100 bars, pressures of less than 20 bars being preferred.

The reaction temperature is generally between 90° and 300° C., preferably between 160° and 230° C. High temperatures, although uneconomic, are not impossible in view of the only very slightly corrosive character of the anhydrous reaction medium and in view of the fact that the solvents used only build up low pressures at these temperatures.

The noble metals forming the base of the catalysts used in the invention are metals from group VIII of the periodic classification, such as ruthenium, rhodium, palladium, osmium, iridium and platinum; palladium is the preferred metal. The metal can be in the metallic form or in the form of a chemical compound; generally, it is preferred for the metal to be used in the metallic form.

The catalyst can be supported or unsupported. Any support which is in itself known for supporting catalysts can be used as the catalyst support, provided that it is resistant to the medium and to acids; particularly suitable supports which may be mentioned are active charcoal, alumina, silica and barium sulphate; active charcoal is a preferred support. The catalyst and also its support are advantageously in finely divided form; specific surface areas of more than 100 m²/g are generally suitable.

The amount of catalyst used is such that the proportion by weight of noble metal in the catalyst, relative to the compound of the formula (I) to be treated, is generally between 0.01 and 15%, preferably between 0.5 and 10%.

Furthermore, the noble metal can be associated with another metal co-deposited with it on the support. This second metal belongs to groups 1b to 5a of the periodic classification. Bismuth, lead, tin, thallium, mercury and silver may be mentioned in particular. It has found, in particular, that good results are obtained using silver.

The following may preferably be mentioned as compounds of the formula (I) capable of being treated by the process of the invention: 2,3-dichloroaniline, 2,5-dichloroaniline, 3,4-dichloroaniline, 2,3,4-trichloroaniline, 2,3,5-trichloroaniline, 2,3,6-trichloroaniline, 2,4,5-trichloroaniline, 3,4,5-trichloroanline, 2,3,4,6-tetrachloroaniline, 2,3,4,5-tetrachloroaniline, 2,3,5,6-tetrachloroaniline and pentachloroaniline, and also: 4,5,6-trichloro-2-methylaniline, 2,5-dichloro-4-methylaniline, 2,3,5,6-tetrachloro-4-methylaniline, 2,5-dichloro-4-ethylaniline, 2,5-dichloro-4-propylaniline, 3,4,6-trichloro-2-benzylaniline, 2,2'-diamino-3,5,6,3',5',6'-hexachlorodiphenylmethane, 2-amino-3,4,5-trichlorobiphenyl, 4,4'-diaminooctachlorobiphenyl, 4,5-dichloro-2-methoxyaniline, 3,4-dichloro-2-methoxyaniline, 3,6-dichloro-2-methoxyaniline, 5,6-dichloro-2-methoxyaniline, 4,5,6-trichloro-2-methoxyaniline, 3,4,6-trichloro-2-methoxyaniline, 3,4,5-trichloro-2-methoxyaniline, 3,4,5,6-tetrachloro-2-methoxyaniline, 4,5-dichloro-3-methoxyaniline, 2,5-dichloro-3-methoxyaniline, 5,6-dichloro-3-methoxyaniline, 4,5,6-trichloro-3-methoxyaniline, 2,4,5,6-tetrachloro-3-methoxyaniline, 2,3-dichloro-4-methoxyaniline, 2,5-dichloro-4-methoxyaniline, 2,3,6-trichloro-4-methoxyaniline, 2,3,5-trichloro-4-methoxyaniline, 2,3,5,6-tetrachloro-4-methoxyaniline, 4,5-dichloro-2-phenoxyaniline, 3,4,5,6-tetrachloro-2-phenoxyaniline, 2,5-dichloro-4-phenoxyaniline and 2,3,5,6-tetrachloro-4-phenoxyaniline.

The following may preferably be mentioned amongst the anilines substituted in the meta-position by the chlorine atom and capable of being prepared by the process according to the invention: meta-chloroaniline and 3,5-dichloroaniline, and also 5-chloro-2-methylaniline, 5-chloro-3-methylaniline, 3-chloro-4-methylaniline, 3,5-dichloro-4-methylaniline, 5-chloro-3,4-dimethylaniline, 3-chloro-4-ethylaniline, 3-chloro-2-benzylaniline, 4,4'-diamino-2,6,2',6'-tetrachlorobiphenyl, 3-chloro-2-methoxyaniline, 5-chloro-2-methoxyaniline, 3,5-dichloro-2-methoxyaniline, 3-chloro-4-methoxyaniline, 4-chloro-3-methoxyaniline, 3,5-dichloro-4-methoxyaniline, 3-chloro-2-phenoxyaniline, 5-chloro-2-phenoxyaniline, 3,5-dichloro-2-phenoxyaniline and 3,5-dichloro-4-phenoxyaniline.

The process according to the invention can be carried out continuously or batchwise. At the end of the reaction, the catalyst can be separated off, if necessary, by filtration or by equivalent means such as draining; the meta-chloroaniline prepared can be separated off by any means which is in itself known, e.g. by solvent extraction and/or by distillation.

The process according to the invention is very advantageous because it makes it possible to obtain meta-chloroanilines under excellent conditions of selectivity, at moderate temperatures and under moderate pressures, without fear of substantial corrosion or of premature wear of the equipment.

The examples which follow, which are given without implying a limitation, illustrate how the process according to the invention is carried out and the results obtained.

EXAMPLE 1

The following are introduced into a 125 cc stainless steel autoclave:
3,4,5-trichloroaniline ($4 \times 10^{-3}$ mol),
1,2,4-trichlorobenzene (20 ml) and
a catalyst consisting of palladium deposited on active charcoal (specific surface area: 1,300 m²/g, proportion by weight of palladium: 5%) (0.2 g).

The oxygen is removed from the autoclave by purges with nitrogen and then with hydrogen. HCl ($4 \times 10^{-3}$ mol) is subsequently introduced from a supply containing anhydrous hydrochloric acid under pressure, and the pressure in the autoclave is then brought to 9 bars (at ambient temperature) with hydrogen. The autoclave is heated to 210° C. and the mixture is left to react for 6 hours at this temperature. The pressure rises to about 15 bars. The autoclave is then cooled, degassed and emptied. The reaction mixture is treated with water to which sodium hydroxide has been added in an amount such that all the hydrochloric acid present (dissolved or combined with the polychloroanilines) is neutralized.

The catalyst is filtered off and washed with water and trichlorobenzene.

The organic phase is analyzed by vapor phase chromatography.

Under these conditions, it is observed that the degree of conversion of the 3,4,5-trichloroaniline is 100% and the yield of 3,5-dichloroaniline is 96.5%. 3.5% of 3-chloroaniline was also formed. The degree of dechlorination of the solvent is 0.16 mol% of HCl, relative to the solvent.

EXAMPLE 2

Example 1 is repeated under 20 bars of hydrogen (measured at ambient temperature), i.e. about 35 bars at 210° C. For a degree of conversion of 100% of the 3,4,5-trichloroaniline, the yield of 3,5-dichloroaniline is 97.9% and the yield of 3-chloroaniline is 2.1%. The degree of hydrodechlorination of the solvent is 0.16%.

EXAMPLE 3

Example 1 is repeated except that $40 \times 10^{-3}$ mol of anhydrous HCl is introduced and 23 bars of $H_2$, measured at ambient temperature (the pressure at 210° C. is of the order of 40 bars), are introduced. The degree of conversion of the 3,4,5-trichloroaniline is 100%. The yield of 3,5-dichloroaniline is 99% and the yield of meta-chloroaniline is 1%. The degree of hydrodechlorination of the solvent is 0.06%.

EXAMPLE 4

Example 2 is repeated, the 3,4,5-trichloroaniline being replaced by 2,3,4,5-tetrachloroaniline and 0.4 g of the same 5% strength Pd catalyst being used in place of 0.2 g. After a reaction time of 10 hours under the conditions of Example 2, the degree of conversion of the 2,3,4,5-tetrachloroaniline is 100%. The yield of 3,5-dichloroaniline is 98.5% and the yield of 3-chloroaniline is 1.5%. The degree of hydrodechlorination of the solvent is 0.06%.

EXAMPLE 5

The procedure is as stated in Example 1. The charges are as follows:
3,4,5-trichloroaniline ($4.0 \times 10^{-3}$ mol),
1,2,4-trichlorobenzene (20 ml),
5% strength Pd-on-charcoal catalyst (0.2 g) and
anhydrous iodine ($5.0 \times 10^{-5}$ gram atom).

No further hydrochloric acid is introduced and the autoclave is placed under a pressure of 5 bars with hydrogen (measured under ambient conditions), i.e. about 9 bars at 210° C. After a reaction time of 8 hours at 210° C., a yield of 96.8% of 3,5-dichloroaniline, relative to the 3,4,5-trichloroaniline converted, is obtained for a degree of conversion of 94.6%. The degree of hydrodechlorination of the solvent is 0.02%.

EXAMPLE 6

The procedure is as in Example 5, but $5 \times 10^{-3}$ gram atom of iodine is used. After a reaction time of 7 hours at 210° C., a yield of 98.8% of 3,5-dichloroaniline is obtained for a complete degree of conversion. There is no hydrodechlorination of the solvent.

EXAMPLE 7

Example 1 is repeated, the 3,4,5-trichloroaniline being replaced by 2,3,5,6-tetrachloroaniline. The following are introduced:
2,3,5,6-tetrachloroaniline ($4.0 \times 10^{-3}$ mol),
5% strength Pd-on-C catalyst (0.25 g),
1,2,4-trichlorobenzene (20 ml) and
anhydrous hydriodic acid ($6.2 \times 10^{-3}$ mol).

The autoclave is placed under a pressure of 6 bars of hydrogen, measured under ambient conditions, and the mixture is left to react for 10 hours at 210° C. (the pressure rises to 11 bars at 210° C.). The treatment and the analysis of the experiment are carried out as stated in Example 1. For a complete degree of conversion of the 2,3,5,6-tetrachloroaniline, a yield of 99.9% of 3,5-dichloroaniline is obtained. The degree of hydrodechlorination of the solvent is 0.05%.

EXAMPLE 8

Example 7 is repeated, $16.0 \times 10^{-3}$ mol of HI being introduced in place of $6.2 \times 10^{-3}$ mol. After a reaction time of 2 hours under these same conditions, the degree of conversion of the 2,3,5,6-tetrachloroaniline is 98.5%. 3,5-Dichloroaniline is obtained with a yield of 98.7%, relative to the 2,3,5,6-tetrachloroaniline converted. The degree of hydrodechlorination of the solvent is 0.1%.

EXAMPLE 9

In an experiment carried out as in Example 1, the following are introduced into a 250 ml stainless steel autoclave:
3,4,5-trichloroaniline (0.0125 mol),
1,2,4-trichlorobenzene (20 ml),
Pd-on-C catalyst containing 5% of Pd (0.1 g),
anhydrous hydrobromic acid ($8 \times 10^{-3}$ mol) and
5 bars of hydrogen, measured under ambient conditions (i.e. about 9 bars at 210° C.).

After a reaction time of 5 hours at 210° C., a yield of 99% of 3,5-dichloroaniline was obtained for a complete degree of conversion of the 3,4,5-trichloroaniline. The degree of hydrodechlorination of the solvent is zero.

EXAMPLE 10

Example 9 is repeated, the 3,4,5-trichloroaniline being replaced by 3,4-dichloroaniline. After a reaction time of 7 hours under the same conditions, 3-chloroaniline is obtained with a yield of 100% for a degree of conversion of 100% of the 3,4-dichloroaniline. The degree of hydrodechlorination of the solvent is 0.09%.

EXAMPLE 11

Example 9 is repeated, the 3,4,5-trichloroaniline being replaced by 2,3-dichloroaniline. After a reaction time of 28 hours under the same conditions, 3-chloroaniline is obtained with a yield of 100% for a degree of conversion of 100% of the 2,3-dichloroaniline. The degree of hydrodechlorination of the solvent is 0.09%.

EXAMPLE 12

Example 9 is repeated, the 3,4,5-trichloroaniline being replaced by 2,4,5-trichloroaniline and 0.5 g of the same catalyst being introduced in place of 0.1 g. After a reaction time of 10 hours under the same conditions, 3-chloroaniline is obtained with a yield of 100% for a complete conversion of the 2,4,5-trichloroaniline and of the intermediates (2,5-, 2,3- and 3,4-dichloroanilines). The degree of hydrodechlorination of the solvent is 0.09%.

EXAMPLE 13

The following are introduced into a 225 cc stainless steel autoclave:
3,4,5-trichloroaniline ($1 \times 10^{-3}$ mol),
1,2,4-trichlorobenzene (40 ml) and
a catalyst consisting of palladium deposited on active charcoal (specific surface area: 1,300 m²/g, proportion by weight of palladium: 5%) (0.8 g).

The procedure is then as in Example 1, except that $2 \times 10^{-3}$ mol of HCl is introduced and except that the mixture is heated at 160° C. for 10 hours, with stirring.

Under these conditions, it is observed that the degree of conversion of the 3,4,5-trichloroaniline is 100% and the yield of 3,5-dichloroaniline is 96.5%. 2% of 3-chloroaniline was also formed.

EXAMPLE 14

The following are introduced into a 225 cc stainless steel autoclave:
2,3-dichloroaniline (0.028 mol),
3,4-dichloroaniline (0.012 mol),
1,2-dichlorobenzene (40 ml),
a solution of hydriodic acid containing 0.77 mol in the above 1,2-dichlorobenzene (0.45 ml; i.e. $0.35 \times 10^{-3}$ mol of HI) and
the catalyst described in Example 13 (0.32 g).

5 bars of hydrogen are introduced at ambient temperature and the mixture is then heated to 206° C. At equilibrium, the total pressure is 12 bars. The reaction is then left to proceed for 15 hours 30 minutes.

The autoclave is then cooled and degassed. The reaction mixture is hydrolyzed/neutralized with an aqueous solution of sodium hydroxide (10 mols/liter) and the organic phase is analyzed by vapor phase chromatography.

Under these conditions, it is observed that the degree of conversion of the 3,4-dichloroaniline is 100% and the degree of conversion of the 2,3-dichloroaniline is 62%. The yield of 3-chloroaniline, relative to the dichloroanilines converted, is 99.9%.

I claim:

1. A process for the preparation of anilines substituted in the meta-position by a halogen atom, by the catalytic hydrogenation, in an anhydrous organic liquid phase, under the action of heat and under pressure, in the presence of noble metals from group VIII of the periodic classification, of amine-substituted and halogen-substituted benzene derivatives of the formula:

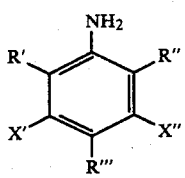

in which:
X' and X", which are identical to or different from one another, each represent a halogen atom, an alkyl radical having 1 to 4 carbon atoms or an alkoxy radical having 1 to 4 carbon atoms, at least one of X' and X" necessarily being a halogen atom, and one of X' and X" may represent hydrogen, and
R', R" and R'", which are identical to or different from one another, each represent a halogen atom, an alkyl radical having 1 to 4 carbon atoms, alkoxy radical having 1 to 4 carbon atoms, an optionally substituted phenyl, benzyl or phenoxy radical, at least one of these three symbols representing the halogen atom, and at most two of R', R" and R'"may represent hydrogen,
wherein the hydrogenation reaction is carried out in the presence of a halogen-containing hydracid, or of a generator of this acid, in a chlorobenzene solvent.

2. The process according to claim 1, wherein the halogen-containing hydracid is hydrochloric acid.

3. The process according to claim 1, wherein the halogen-containing hydracid is hydrobromic acid.

4. The process according to claim 1, wherein the halogen-containing hydracid is hydriodic acid.

5. The process according to one of claims 1 to 4, wherein the halogen-containing hydracid is in a molar ratio to the starting polychloroaniline of between 1/100 and 10/1.

6. The process according to claim 5, wherein the hydracid is in a molar ratio to the starting polychloroaniline of between 1/10 and 5/1.

7. The process according to claim 1, wherein said reaction is carried out in the presence of the hydracid generator iodine.

8. The process according to claim 1, wherein the solvent is chlorobenzene.

9. The process according to claim 1, wherein the solvent is chosen from the group comprising 1,2-dichlorobenzene and 1,3-dichlorobenzene.

10. The process according to claim 1, wherein the solvent is 1,2,4-trichlorobenzene.

11. The process according to claim 1, in which R', R", R'", X' and X", which are identical to or different from one another, represent the hydrogen atom or the chlorine atom.

12. The process for the preparation of optionally substituted meta-dichloroanilines according to claim 1, in which X' and X" represent the chlorine atom.

13. The process for the preparation of optionally substituted meta-monochloroanilines according to claim 1, in which only one of the two radicals X' and X" is the chlorine atom.

14. The process for the preparation of 3,5-dichloroaniline according to claim 1, in which:
X' and X" are the chlorine atom and
R', R" and R'" are the hydrogen atom or the chlorine atom.

15. The process according to claim 1, wherein the total pressure is between 5 and 100 bars.

16. The process according to claim 15, wherein the total pressure is between 5 and 20 bars.

17. The process according to claim 1, wherein the reaction is carried out at a temperature of between 90° and 300° C.

18. The process according to claim 1, wherein the catalyst is palladium.

19. The process according to claim 1, wherein the proportion by weight of noble metal, relative to the compound of the formula (I), is between 0.01 and 10%.

20. The process according to claim 1 wherein each of said halogen atoms is a chlorine atom.

21. The process according to claim 1 wherein the reaction is carried out in the presence of a hydracid selected from hydrochloric acid, hydrobromic acid and hydroiodic acid.

22. The process according to claim 21 in which the solvent is chosen from the group consisting of chlorobenzene, 1,2-dichlorobenzene, 1,3-dichlorobenzene and 1,2,4-trichlorobenzene.

23. The process according to claim 1 wherein the reaction is carried out at a temperature of between 150° and 230° C.

24. The process according to claim 1 wherein the proportion by weight of noble metal relative to the compound of formula I is between 0.1 and 5%.

25. The process according to one of claims 1, 21 or 22 wherein the reaction is carried out under a total pressure of between 5 and 100 bars, at a temperature of 90° to 300° C. and in the presence of a palladium catalyst in an amount of 0.01 to 10% relative to the compound of formula (I), and wherein the molar ratio of the halogen-containing hydracid to the compound of formula 1 is between 1/100 and 10/1.

26. The process according to one of claims 1, 21 or 22 wherein the reaction is carried out under a total pressure of between 5 and 20 bars, at a temperature of between 150° and 230° C. and in the pressence of a palladium catalyst in an amount of 0.1 to 5% relative to the compound of formula I, and wherein the molar ratio of the halogen containing hydracid and the compound of formula I is between 1/10 and 5/1.

* * * * *